US00PP25465P3

(12) United States Plant Patent
Sparks

(10) Patent No.: US PP25,465 P3
(45) Date of Patent: Apr. 28, 2015

(54) PECAN TREE NAMED 'HUFFMAN'

(50) Latin Name: *Carya illinoinensis*
Varietal Denomination: Huffman

(71) Applicant: University of Georgia Research Foundation, Inc., Athens, GA (US)

(72) Inventor: Darrell Sparks, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 116 days.

(21) Appl. No.: 13/987,385

(22) Filed: Jul. 19, 2013

(65) Prior Publication Data

US 2015/0026849 P1 Jan. 22, 2015

(51) Int. Cl.
*A01H 5/00* (2006.01)

(52) U.S. Cl.
USPC ..... Plt./153

(58) Field of Classification Search
USPC ..... Plt./153
See application file for complete search history.

*Primary Examiner* — Anne Grunberg
(74) *Attorney, Agent, or Firm* — Klarquist Sparkman, LLP

(57) ABSTRACT

A pecan tree distinguished by the following unique combination of characteristics: Consistent and acceptable fruit production, small fruit cluster, moderately early nut maturity, large nut producing mammoth kernels with good color and no observed speckling, and no observed scab fungus.

3 Drawing Sheets

Latin name of the genus and species of the plant: *Carya illinoinensis.*

Variety denomination: 'Huffman'.

BACKGROUND OF THE INVENTION

The present invention relates to a new and distinct variety of pecan tree named 'Huffman'. My new tree can be used in gardens or for commercial production of pecan nuts. This new tree was selected from seedlings grown from controlled pollination at the University of Georgia Horticulture Farm in Watkinsville, Ga., in 1990. The 'Huffman' selection resulted from crossing 'Desirable' (unpatented) as the seed parent with 'Pawnee' (unpatented) as the pollen parent. The resulting tree was selected when growing in a cultivated area at Watkinsville, Ga.

BRIEF SUMMARY OF THE INVENTION

'Huffman' is distinguished from other pecan varieties known to the inventor due to the following unique combination of characteristics: Consistent and acceptable fruit production, small fruit cluster, moderately early nut maturity, large nut producing mammoth kernels with good color and no observed speckling, and no observed scab fungus.

Asexual reproduction of 'Huffman' by grafting, (top working) onto 'Desirable' pecan trees in 2005 and 2008 at a location in Albany, Ga. and in 2009 at a location in Leary, Ga. was performed in order to evaluate these trees. Asexual reproduction of 'Huffman' has shown that the forgoing characteristics come true to form, are firmly fixed, and are established and transmitted through succeeding propagations.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

Figure 1:
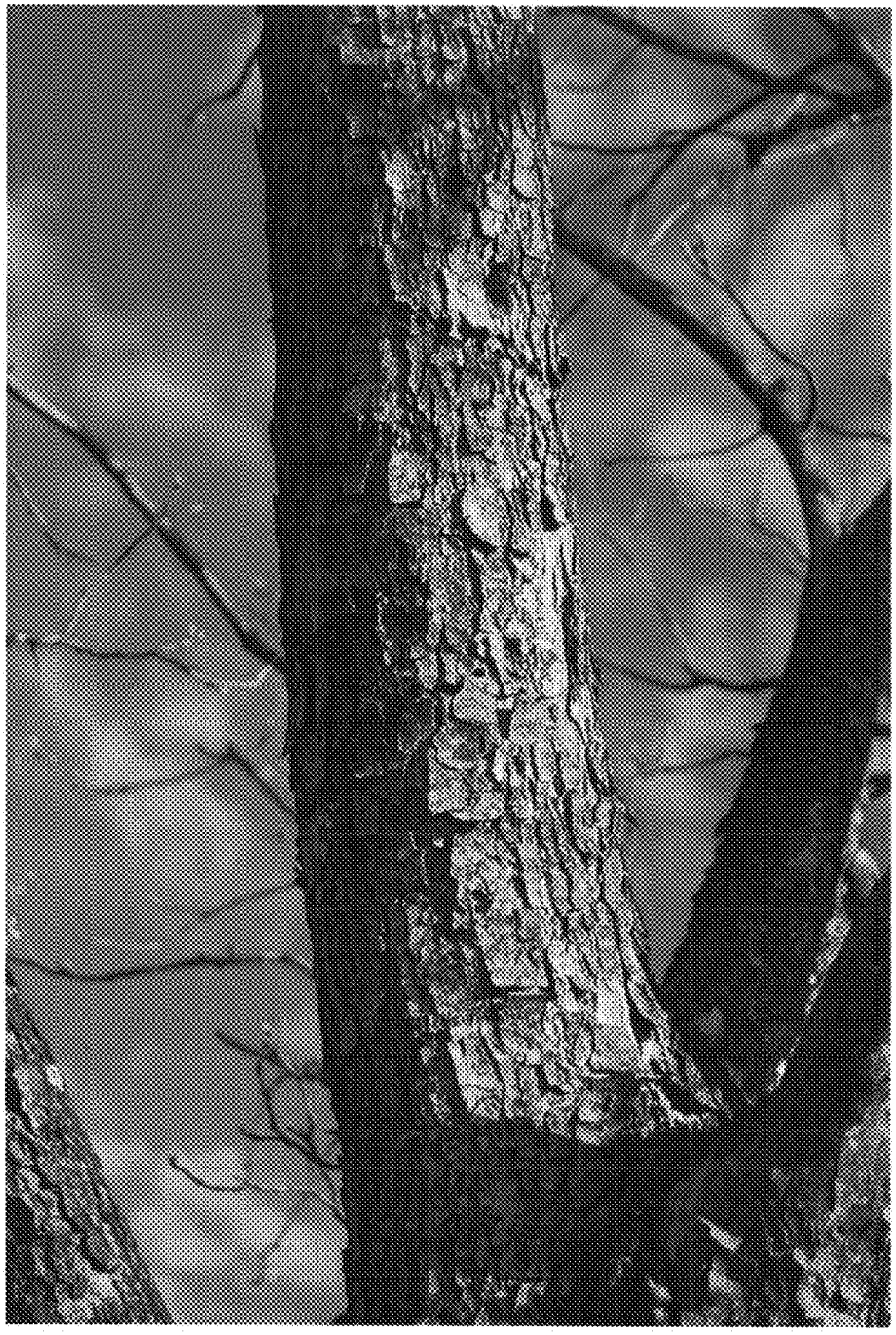
FIG. 1 is a photograph showing scaly bark of 'Huffman'.
Figure 2:
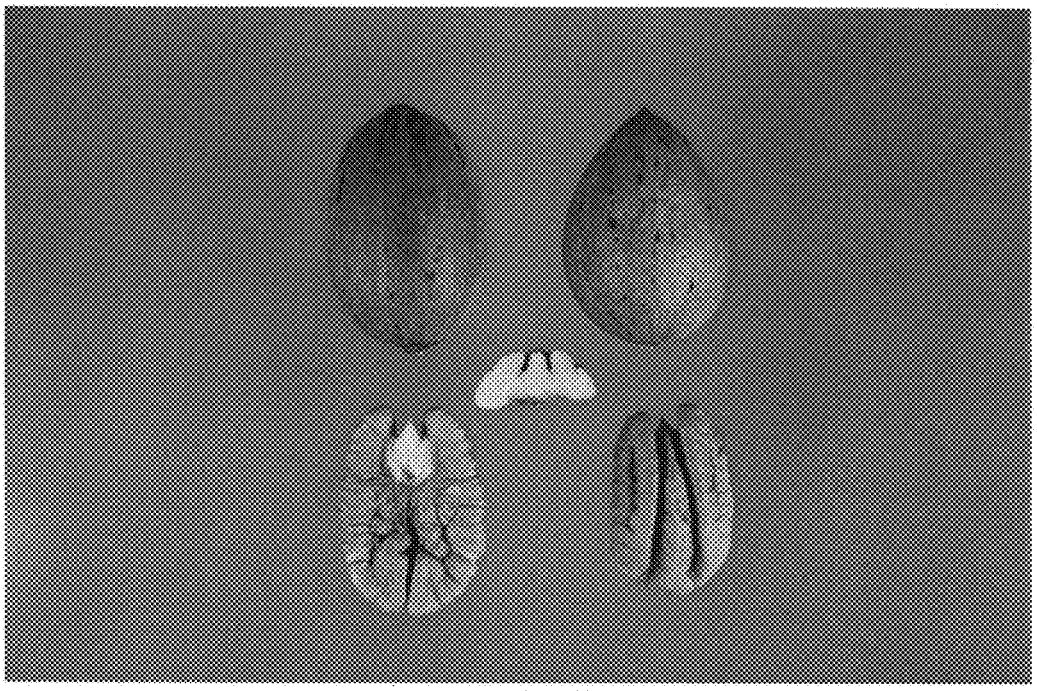
FIG. 2 is a photograph showing nut shape and kernel characteristics of 'Huffman'. The top views show, from left to right, the suture side and non-suture side of the nut. Also, the bottom views show, respectively from left to right, the ventral side of the kernel, a cross-section of the kernel with the dorsal side up, and the dorsal side of the kernel.

The colors of an illustration of this type may vary with lighting and other conditions. Therefore, color characteristics of this new variety should be determined with reference to the observations described herein, rather than from these illustrations alone.

DETAILED DESCRIPTION

Botanical

The following detailed description of 'Huffman' is based on observations of the original tree growing in Watkinsville, Ga. and of asexually reproduced progeny growing in Albany, Ga. and Leary, Ga.

Varietal Name: 'Huffman'.

Parentage:

*Seed parent.*—'Desirable'.

*Pollen parent.*—'Pawnee'.

Tree:

*Overall shape.*—Upright, moderately spreading, height to width ratio is about 1.1.

*Vigor.*—Vigorous, prolific, 'Huffman' fruited the second year after grafting (top working) onto 'Desirable' trees, and has done so in subsequent years. Original tree fruited 10 years from seed.

*Height.*—Of original tree, about 13 meters.

*Width.*—Of original tree, about 12 meters.

*Trunk.*—Of original tree (measured ½ meter above ground level) about 0.4 m circumference.

*Trunk bark texture.*—Scaly as mature tree.

*Trunk bark color.*—Grey (RHS 202B).

*Patches.*—Trunk characteristically has holes pecked by yellow bellied sapsucker.

*Branch color.*—Branch shoots in woody stage are Grey-brown (RHS 199A) in color, with Grey-brown lenticels (RHS 199D) that are elongated and about 1 mm long by 0.05 mm wide.

*Internodes.*—Average internode length is about 2.0 cm, between the $3^{rd}$ and $4^{th}$ leaf on a shoot.

*Bearing.*—Consistent annual production.

*Disease and insect resistance.*—Apparent immunity to scab *Fusicladosporium effusumi* (G. Winters) Partridge & Morgan-Jones. Susceptible to southern pecan leaf *phylloxera* (*Phylloxera russellae* stoetzel) at one low insecticide usage orchard but not at others. Susceptible to potato leaf hopper (*Empoasca fabae* Harris), but with insignificant damage. Resistance to black pecan aphid *Melanocallis caryaefoliae* (Davis) is high.

Leaves: The mature leaf is odd pinnate compound, deciduous with leaflets having a dark green upper surface and a lighter green lower surface. Each mature leaf has from 11 to 15 leaflets. Leaflets droop from the rachis. Droop is slight on basal leaves but increases progressively and substantially from basal to apical leaves on the shoot.

*Size of mature leaf* (*fourth leaf from base*).—34.1 cm long, 19.6 cm wide.

*Peduncle.*—Round in cross-section, tan in color (RHS 199B). The length of the peduncle of the fourth leaf from the base is about 5.2 cm. The diameter of the peduncle of the fourth leaf from the base is about 2.6 mm.

*Leaflet.*—Size and shape: Fourth leaflet on fourth leaf from base 10.4 cm long by 3.7 cm wide. Falcate in shape. Base oblique. Margin serrate. Leaflets are non convoluted on mature trees but on young vigorous trees convolution increases from basal to apical leaves on the shoot. Texture: Smooth. Sheen: Glossy. Petiole: Sessile. Margin: Serrate. Tip shape: Acuminate and narrow. Leaflet color: Upper leaf surface: Dark green (RHS 139A). Lower leaf surface: Green (RHS 138A). Pubescence: Upper leaf surface is not pubescent. Lower surface is pubescent. The length, width and other measurements were obtained from observations of a typical leaf.

Inflorescence:

*General.*—The 'Huffman' pecan is monoecious, anemophilous, and protandrous.

*Flowers.*—Pistil flowers are borne on a determinate spike, with staminate flowers borne on a determinate pendulous catkin. Two-five individual pistillate flowers per spike, borne alternately on terminally-positioned spikes. The pistillate flower is symmetrical with no stamens or petals. The pedicels are sessile. The staminate or catkin length is 77 mm and width is 4.9 mm. The staminate color is Green (RHS 144B) with gold pollen (RHS 3A). The involucre size, which includes the stigma, is 5.9 mm long by 2.1 mm wide. The flower has one pistil with a oxblood red (RHS 61A) stigma. The flower has four bracts, which are green (RHS 144A), lanceolate, 5.1 mm long by 1.1 mm wide and are fused at the bases, forming a copular involucre.

Fruit: Mature fruit is dehiscent.

*Shuck.*—Green (RHS 144B) but russet near maturity.

*Fruit split during water stage.*—Not observed to be a problem.

*Shuck decline.*—Shuck dieback during kernel formation has not been observed to be a problem.

Nuts: (Observations from a limited number of typical nuts from several growing seasons in Watkinsville, Ga.).

*Size.*—Large, length about 38 mm, width about 25 mm (width measurement taken midway along the length of the nut and across sutures); length to width ratio about 1.5. Nut flatness (ratio of width across sutures to width between sutures) is about 1.0.

*Form.*—Oblong with a round base, apex that is obtuse and cuspidate to cuspidate asymmetric, with a slightly grooved apex.

*Sutures.*—Subtle, non-elevated.

*Dorsal grooves.*—Wide, thereby decreasing the percentage kernel in the nut.

*Weight.*—11.9 grams per nut (non-limiting soil moisture).

*Cluster size.*—About 1.7 fruits per cluster.

*Texture.*—Faint ridges.

*Shell thickness.*—Thin, 0.77 mm.

*Kernel color.*—Good color, Greyed-orange (RHS 165B).

*Kernel coat.*—No speckling has been observed.

*Kernel percentage of nut.*—About 57.2 percent.

*Nut maturity.*—October 6th. Later than 'Byrd' (U.S. Plant Pat. No. 20,867) by about 14 days.

*Harvestability.*—Suitable for machine harvest.

*Cracking/shelling ability.*—Cracks exceptionally well, percentage of kernels with intact halves is high. Typically, less than five percent of chipped or broken kernels were observed.

COMPARISONS TO OTHER VARIETIES

The form of 'Huffman' trees is moderately spreading and similar to the 'Desirable' parent. Thus, 'Huffman' is less upright than 'Byrd'. The timing of bud break of 'Huffman' is similar to 'Morrill' (U.S. Plant Pat. No. 23,335) and 'Stuart' (unpatented) pecan trees but later than many pecan cultivars. Thus, 'Huffman' is less susceptible to late-spring freezes in Georgia than most other pecan cultivars. The leaves of 'Huffman' are forest green, as in 'Pawnee', but unlike the pale color 'Desirable'. Leaflet orientation of 'Huffman' leaves is similar to parent 'Desirable' and most pecan genotypes; that is leaflets droop from the rachis and is unlike parent 'Pawnee' where the opposite leaflets are oriented at 180 degrees relative to each other. Leaflet margins of mature 'Huffman' trees are not convoluted. The stigmatic surface of 'Huffman' is oxblood (RHS 61A), similar to the oxblood color of both parents and in contrast to the green stigma of 'Wichita'. 'Huffman' appears to be immune to the scab fungus as none has yet been observed and contrasts with the high susceptibility to scab fungus of both parents and to almost all other pecan cultivars. In the humid southeastern United States, this apparent immunity to scab fungus is a major attribute of 'Huffman'. Mature bark is often pecked by yellow bellied sapsucker as in 'Stuart'

(unpatented) and 'Wichita' (unpatented). In the tables below, 'Cheyenne', 'Elliot' and 'Schley' are unpatented varieties. Also, the 'Cunard' variety is the subject of U.S. Plant Pat. No. 24,373 and the 'Treadwell' variety, the subject of pending U.S. Plant patent application Ser. No. 13/987,384.

TABLE 1

Approximate periods of pollen shedding and stigma receptivity for 'Huffman' and selected other pecan cultivars in May, Watkinsville, Georgia.

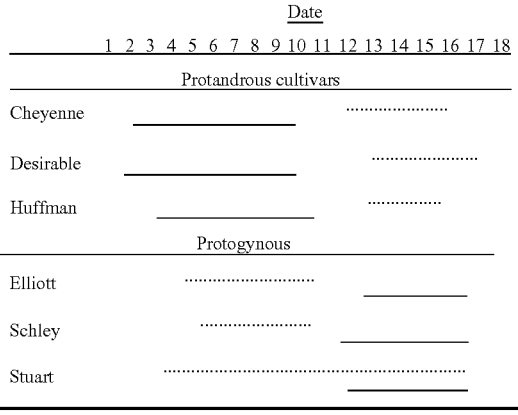

..... = Period of stigma receptivity.

_____ = Period of pollen shedding.

Tables 2 and 3 below compare the characteristics of nuts from 'Huffman' with nuts of other pecan cultivars.

declines as the harvest becomes later. Consequently, cultivars that exhibit early maturity at harvest are commercially important. The color of a kernel's seed coat (lighter is preferred), and the percentage kernel of the nut also affects the selling price of pecans. Although the nut maturity of 'Huffman' is about 14 days later than nut maturity of 'Byrd', it is about 15 days earlier than the 'Desirable' cultivar (unpatented). 'Desirable' is believed to be the leading cultivar now being planted in new orchards in Georgia. Even though the nut maturity of 'Huffman' is later than 'Byrd', the maturity date is still early enough to be considered an early market cultivar. The later harvest date of 'Huffman' is advantageous in one respect because a number of growers of pecans in southwest Georgia also grow peanuts. The harvest date of 'Byrd', 'Pawnee', and 'Treadwell' pecans conflicts with the peanut harvest date. 'Huffman' matures at the end of the peanut harvesting season, making it a more suitable early cultivar for peanut growers that can harvest 'Huffman' pecans following the peanut harvest. In addition to use in a new planting, 'Huffman' is well suited as a replacement tree or as an interplant in a 'Stuart'-'Schley'-'Desirable' orchard, a common combination in the southeastern United States. The nut maturity date of 'Huffman' is similar to the other cultivars allowing a simultaneous harvest of the blended nuts.

From Tables 2 and 3, 'Huffman' nuts are large, equal in size to 'Cunard' and 'Morrill', and larger than 'Desirable', the industry standard for size. Consequently, kernels of 'Huffman' are well suited to the 'mammoth half' market. Nut length is shorter in the case of 'Huffman' nuts than either 'Pawnee' or 'Byrd' nuts and the nut shape is similar. As indicated by the length to width ratio, 'Huffman' nuts are

TABLE 2

Comparison of nut characteristics of 'Byrd', 'Pawnee', 'Morrill', 'Cunard', 'Treadwell', 'Stuart', and 'Huffman' pecan cultivars, Watkinsville, Georgia.

| Cultivar | Wt./nut (g) | Nuts/lb (no.) | Nut length (mm) | Length/width[z] | Nut Flatness ratio[y] | Shell thickness (mm) | Kernel (%) | Nut Maturity date[x] |
|---|---|---|---|---|---|---|---|---|
| 'Byrd' | 7.6 a | 60 a | 41.2 b | 1.83 d | 1.04 bc | 0.64 c | 62.2 b | 22 e |
| 'Pawnee' | 7.4 a | 61 a | 41.2 b | 1.92 c | 0.96 e | 0.77 b | 59.0 c | 18 f |
| 'Morrill' | 8.6 ab | 53 ab | 46.4 a | 2.00 b | 1.14 a | 0.71 b | 65.5 a | 34 bc |
| 'Cunard' | 9.3 b | 49 b | 46.3 a | 2.08 a | 1.02 d | 0.72 b | 61.6 b | 27 d |
| 'Treadwell' | 7.5 ba | 60 ba | 39.2 bc | 1.82 d | 0.98 e | 0.74 b | 59.2 c | 25 de |
| 'Stuart' | 7.6 a | 61 a | 38.8 c | 1.70 e | 1.05 b | 0.91 a | 47.7 d | 39 a |
| 'Huffman' | 9.2 b | 49 b | 38.1 c | 1.54 f | 1.00 de | 0.77 b | 57.2 c | 36 ab |

Means followed by the same letter within a column are not statistically different, $P \leq 0.05$.

[z]Length to width ratio = nut length divided by width. Width was measured midway the length of the nut and across sutures.

[y]Nut flatness ratio = ratio of nut width across sutures to width between sutures. Measurements were made midway the length of the nut.

[x]Date when shuck dehiscence had occurred on 50% of the fruit, from September 1.

TABLE 3

Nut characteristics of 'Desirable' and 'Huffman', Albany, Georgia.

| Cultivar | Wt./nut (g) | Nuts/lb. (no.) | Kernel (%) |
|---|---|---|---|
| 'Desirable' | 9.8 a | 46 b | 55 b |
| 'Huffman' | 11.9 a | 38 a | 56 a |

Means followed by the same letter within a column are not statistically different, $P \leq 0.05$.

Greater nut size and percentage kernel in Albany, Georgia as compared to Watkinsville, Georgia (Table 2) believed due to better irrigation and probably higher temperatures in Albany, Georgia. Soil water was non-limiting at Albany, but not at Watkinsville.

Pecan nuts of large size that mature relatively early command a premium price. The price per pound normally similarly round to 'Pawnee' or 'Byrd' nuts. In cross-section, 'Huffman' and 'Byrd' nuts are near round (flatness ratio 1.00 and 1.04, respectively) while 'Pawnee' nuts are flatter on the suture side than the non-suture side. Referring to Table 2, the shell thickness of 'Huffman' is the same as the shell thickness of 'Pawnee' and thicker than that of 'Byrd'. All three have unusually thin shells, which accounts, in part, for their high percentage kernel. However, the percentage kernel of 'Huffman' nuts is substantially lower than 'Byrd' nuts, and the shells of 'Byrd' nuts are thinner. The higher percentage kernel of 'Byrd' is primarily due its thinner shell. The percentage kernel is a direct function of the shell thickness and the percentage of the shell cavity filled with the kernel. The percentage kernel of 'Huffman' nuts (Tables 2 and 3) is higher than the industry standards, 'Stuart' and 'Desirable'.

Figure 3:
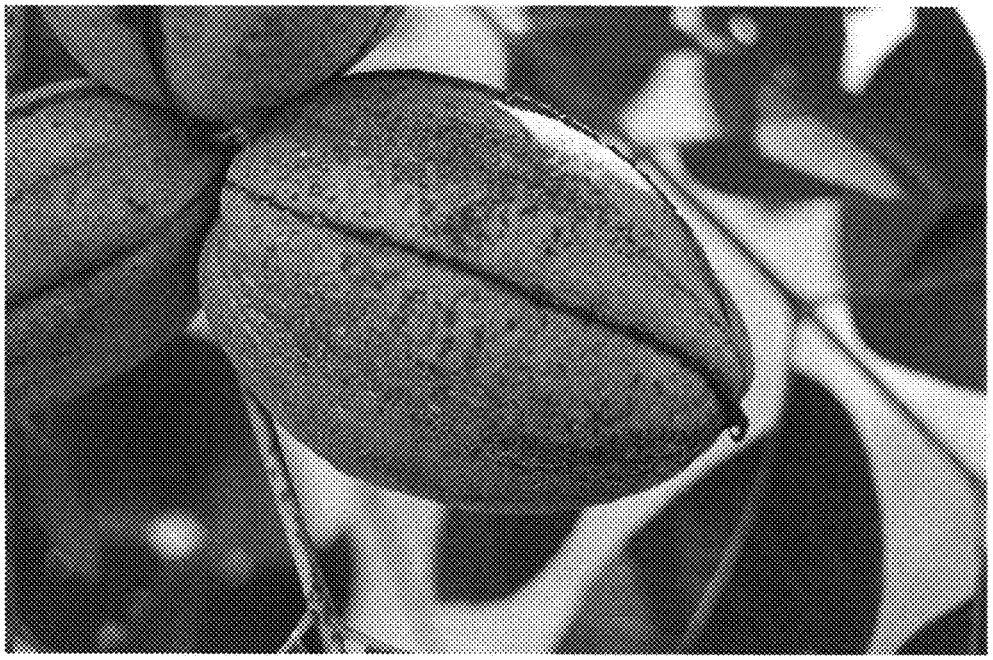
FIG. 3 is a photograph showing shuck characteristics of 'Huffman' pecan near the time of nut maturity.

Under stress, primarily fruiting stress, and when 'Pawnee' pecan trees are grown in humid southeastern United States, the kernel's seed coat can develop conspicuous and unattractive dark spots. This speckling reduces the marketability of these nuts. Speckling has not been observed to be a problem of 'Huffman' nuts grown in Georgia. Kernel color is good (FIG. 3). Kernel color retention is excellent. In addition, unlike the 'Huffman' cultivar, during a heavy "on" nut production year for 'Pawnee' trees growing in Georgia, kernel development is relatively poor, resulting in a high percentage of the nuts being unmarketable or of reduced value.

TABLE 4

Precocity of 'Byrd', 'Cunard', 'Treadwell', 'Morrill', 'Desirable','Huffman', and 'Stuart'.

| Cultivar | Years to initial fruiting [z] |
|---|---|
| 'Cunard' | 2 |
| 'Byrd' | 3 |
| 'Treadwell' | 3 |
| 'Morrill' | 4 |
| 'Desirable' | 4 |
| 'Huffman' | 5 |
| 'Stuart' | >6 |

[z] Years from planting nursery trees.

TABLE 5

Production, nuts per pound, percentage kernel of trees top worked [z] to 'Huffman' and 'Morrill', Albany, Ga., 2010-11.

| Cultivar | lbs./tree | Nuts/lb. (no.) [y] | Kernel (%) [y] |
|---|---|---|---|
| 'Huffman' | 22 a | 38 a | 56.2 b |
| 'Morrill' | 24 a | 39 b | 65.9 a |

Means followed by the same letter within a column are not statistically different, $P \leq 0.05$, n = 4.
[z] Top working simulates a mature tree and allows for earlier evaluation of alternate bearing, kernel development under heavy fruit load, and suitability for mechanical harvest and ease of fruit thinning.
[y] Nut weight is greater and percentage kernel is higher than in Table 3 because of better irrigation.

Table 6 below compares the fruiting characteristics of 'Byrd,' 'Treadwell,' 'Huffman,' 'Cunard,' and 'Morrill' cultivars.

TABLE 6

Fruiting characteristics of 'Byrd', 'Treadwell', 'Huffman', 'Cunard', and 'Morrill', Albany, Georgia.

| Cultivar | Years to fruiting (no.) | Years until alternate bearing (no.) [z] |
|---|---|---|
| 'Byrd' | 2 | 3 |
| 'Treadwell' | 2 | 3 |
| 'Huffman' | 2 | >6 |
| 'Cunard' | 2 | 10 |
| 'Morrill' | 2 | >9 |

[z] Years after top working mature trees to the respective cultivar. Top working simulates a mature tree and allows for earlier evaluation of alternate bearing, kernel development under heavy fruit load, and suitability for mechanical harvest and ease of fruit thinning.

'Huffman' is not precocious and less so than 'Desirable' (Table 4) but is prolific as mature top worked trees and production is good and similar to 'Morrill' (Table 5). In contrast to the precocious 'Byrd' and 'Treadwell', which began to fruit on alternate years 3 years after top working, similar trees of 'Huffman' (Table 6) and the original tree have not borne alternately. Thus, 'Huffman' has annual production as is the case for 'Desirable' and for the same reason, namely a small fruit cluster size (Table 7). 'Huffman' is superior to 'Desirable' in having a larger nut, higher percentage kernel, and no observed (and thus apparent immunity to) scab disease.

TABLE 7

Fruit cluster size of 'Byrd', 'Desirable', 'Morrill', 'Pawnee', 'Cunard', 'Treadwell' and 'Huffman', Watkinsville, Georgia.

| Cultivar | Fruit/cluster (no.) |
|---|---|
| 'Byrd' | 3.1 ab |
| 'Desirable' | 1.5 d |
| 'Morrill' | 2.7 bc |
| 'Pawnee' | 3.1 ab |
| 'Cunard' | 3.4 a |
| 'Treadwell' | 2.7 bc |
| 'Huffman' | 1.7 d |

Means followed by the same letter are not statistically different, $P \leq 0.05$.

Table 8 below compares leaf scab susceptibility of 'Huffman' with 'Byrd', 'Morrill', 'Cunard', 'Treadwell', and 'Desirable'. In addition, 'Pawnee' has been observed to be more susceptible to scab disease than 'Huffman' when grown in Georgia.

TABLE 8

Fruit Scab And Powdery Mildew Susceptibility Of 'Byrd', 'Morrill', 'Cunard','Treadwell', 'Huffman' and 'Desirable'.

| | Leaf scab [x] | |
|---|---|---|
| Cultivar | Leary, 2009 | Watkinsville, 2010 |
| 'Byrd' | 1.0 b | 1.4 b |
| 'Morrill' | 1.3 b | 2.0 b |
| 'Cunard' | 1.3 b | 1.8 b |
| 'Treadwell' | 1.2 b | 1.6 b |
| 'Huffman' | 1.0 b | 1.0 b |
| 'Desirable' | 4.7 a | 3.8 a |

Means followed by the same letter within a column are not statistically different, $P \leq 0.05$.
[x] 1 = no scab lesions; 2 = occasional lesion on leaf, less than 1% of leaves with lesions; 3 = lesions scant on 2 to 10% of leaves; 4 = lesions widespread but no leaf distortion; 5 = lesions widespread and severe leaf distortion.

Table 9 below compares the black pecan aphid resistance of 'Huffman' to the resistance of four other cultivars.

TABLE 9

Black pecan aphid susceptibility of 'Byrd', 'Cunard', 'Desirable', 'Huffman', and 'Morrill', Leary, Georgia.

| Cultivar | Black pecan aphid [z] |
|---|---|
| 'Byrd' | 1.7 ab |
| 'Cunard' | 2.0 a |
| 'Desirable' | 2.2 ab |
| 'Huffman' | 1.0 b |
| 'Morrill' | 2.0 a |

Means followed by the same letter are not statistically different, $P \leq 0.05$.
[z] 1 = no leaf damage, 2 = <1% of leaves with injury, 3 = 1-10% of leaves with injury, 4 = 11-50% of leaves with injury, 5 = >51% of leaves with injury and partial defoliation. Data taken during a year of low aphid population.

In addition, under these humid growing conditions in Georgia, the fruit is highly susceptible to splitting during the "water stage" (liquid endosperm stage) of fruit development. Fruit split can occur following rain and accompanying high humidity in early August in Georgia. Although 'Wichita' has a relatively early nut maturity (7-10 days before 'Stuart') and acceptable nut size (57 nuts per pound), and a kernel percentage of 60-61%, which is higher than the 58-59% of 'Pawnee', because of the susceptibility to scab fungus and splitting it has become a less desirable cultivar for growing in Georgia.

Water split has not been observed in 'Huffman'. The lack of split may be due to the timing of fruit development. Water split is most likely to occur on cultivars when the maximum liquid endosperm stage occurs during the first two weeks in August that often coincides with the rainy period in Georgia. Typically, rainfall in Georgia sharply decreases after August 15th. The maximum liquid endosperm stage in 'Huffman' trees grown in Georgia occurs after August 15th.

The 'Huffman' pecan tree is therefore an improved new and distinct pecan.

I claim:

1. A new and distinct cultivar of pecan tree, substantially as herein illustrated and described.

* * * * *